United States Patent [19]

Latman et al.

[11] Patent Number: 4,795,747

[45] Date of Patent: Jan. 3, 1989

[54] 16-EPIESTRIOL TO PREVENT, INHIBIT OR REDUCE INFLAMMATION

[76] Inventors: Neal S. Latman, 513 Bowie St., Borger, Tex. 79007; Vimal Kishore, 4632 Nottingham Dr., New Orleans, La. 70127; Brent C. Bruot, 620 Woodside Dr., Kent, Ohio 44240

[21] Appl. No.: 62,412

[22] Filed: Jun. 16, 1987

Related U.S. Application Data

[63] Continuation of Ser. No. 812,790, Dec. 23, 1985, abandoned.

[51] Int. Cl.$^4$ .............................................. A61K 31/56
[52] U.S. Cl. .................................................... 514/182
[58] Field of Search ........................................ 514/182

[56] References Cited

PUBLICATIONS

Amer. J. Med. (1983) No. 74, pp. 957–960, article by N. S. Latman.
Hilgar et al from Issue 3, Jun. 1968 from Uterotropic, "Endocyine Bioassoy Data:", Entry Nos. 4324–5902, Part VI, pp. 1–33.
Korenman, Steroids, 13(2):163–177, 1969.
Thomas et al, "Principles of Endocrine Pharmacology", Plenum Medical Book Co., New York, 1986.
Taber's Cyclopedic Medical Dictionary, 15th Edition, p. 576, F. A. Davis Company.
P. H. Jellinck, Bio Chemistry, An Introduction, pp. 280–281, Rinehart and Winston.
Cantarow et al, Biochemistry, Fourth Edition, 1967, p. 689, W. B. Saunders Company.
E. J. W. Barrington, An Introduction to General and Comparative Endocrinology, Second Edition, 1975, p. 111, Clarendon Press.
D. Norris, Vertebrate Endocrinology, Second Edition, 1985, Chapter 9, Lea & Febriger.
R. Chaudhury, Pharmacology of Estrogens, Section 106, pp. 1, 19 and 49, Pergamon Press.
J. Brobeck, Best & Taylor's Physiological Basis of Medical Practice, Tenth Edition, Chapter 10, pp. 7–113, Williams & Wilkins.
E. Selkurt, Physiology, Fifth Edition, p. 651, Little, Brown and Company.
"Dorland's Medical Dictionary", 27th Edition, 1968, p. 584, W. B. Saunders Company.
"Drug Information 86", published by authority of the Board of Directors of the American Society of Hospital Pharmacists, 68:16 Estrogens, p. 1543.
F. Strand, Physiology, A Regulatory Systems Approach, Second Edition, Chapter 25, p. 577, Macmillan Publishing Co.
Merck Index, 10th edition, 1983, entry 3654.
Brandely et al, Biomed. 36:308 (1982).
Espey, L. L., Biol, Reprod. 22:73 (1980).
Siiteri, et al, Ann. N.Y. Acad. Sci, 286:384 (1977).
Ishioka, et al, Acta Endocr. 60:177 (1969).
Toivanen, et al, Med. Pharmacol, Exp. 17:33 (1967).
Hanes, et al, Chapter 63 "The Pharmacol. Basis of Therapeutics", Seventh Ed., MacMillan Publishing Co., N.Y. (1985).

*Primary Examiner*—Leonard Schenkman
*Assistant Examiner*—Joseph A. Lipovsky
*Attorney, Agent, or Firm*—Harold H. Flanders; Robert L. Price

[57] ABSTRACT

16-epiestriol as an anti-inflammatory drug.

4 Claims, 1 Drawing Sheet

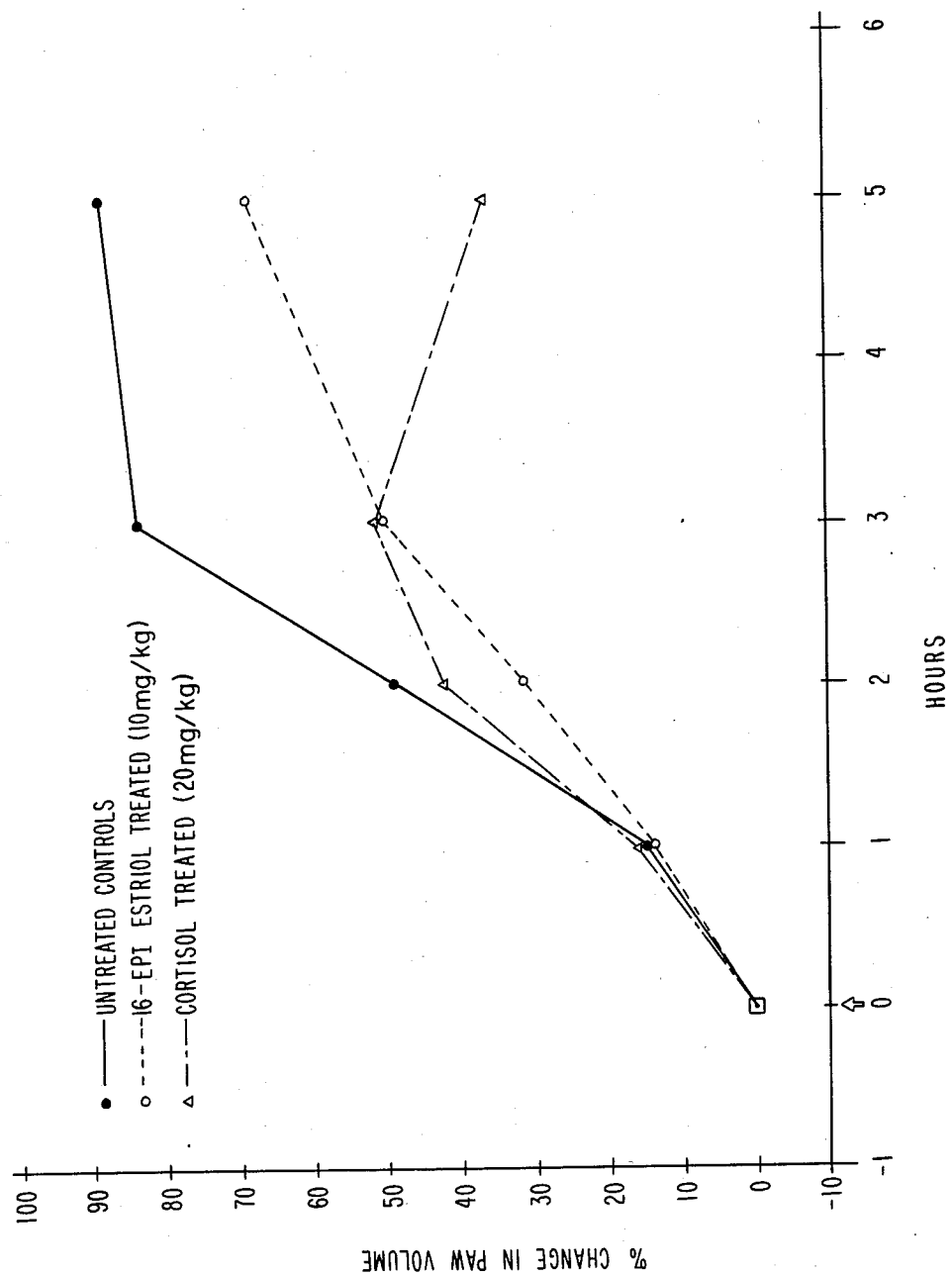

16-EPIESTRIOL TO PREVENT, INHIBIT OR REDUCE INFLAMMATION

This application is a continuation of application Ser. No. 812,790, filed Dec. 23, 1985, now abandoned.

FIELD OF THE INVENTION

The present invention relates to the discovery that 16-epiestriol has a high anti-inflammatory potency and may be employed in the symptomatic relief of rheumatoid arthritis and other diseases with an inflammatory component.

BACKGROUND

In a recent article (Latman, N. S. 1983, Amer. J. Med. 74: 957–960), one of the co-inventors of the present application, provides a review of the evidence which suggests possible anti-inflammatory activity of some of the sex steroid hormones, progesterone and some of the estrogens. Specifically the observations included the fact that the symptoms of rheumatoid arthritis are significantly reduced during the post-ovulatory phase of the menstrual cycle; that pregnancy usually results in symptomatic relief of rheumatoid arthritis; that there is a reduction in the incidence of rheumatoid arthritis by approximately 50% in women taking an oral contraceptive; and that progesterone and some of the estrogen treatments reduce symptoms of inflammation and arthritis in several animal models. It was thus suggested that progesterone and at least some of the estrogens may exhibit anti-inflammatory activity. This activity is believed to be associated with molecular structural characteristics, but the problem remains to identify the structural characteristics which are effective within certain steroidal hormones and their metabolites and derivatives which may exhibit a high degree of anti-inflammatory activity with a minimum of estrogenic and/or mineralocorticoid activity.

A number of steroids have been tested over the years as possibly having some anti-inflammatory effects, with many being ultimately found to have little or no anti-inflammatory effect. In short, it has been long recognized that the fact that a chemical may be a steroid is not necessarily an indication that it may have any anti-inflammatory effect. Example of steroids which appear to exhibit no anti-inflammatory activity or may exhibit pro-inflammatory activity include aldosterone, 11-deoxycorticosterone (Bentley, P. J. "Endocrine Pharmacology" 1980. Cambridge University Press, Cambridge), 11-desoxycortisol, and tetrahydrocortisol (Haynes, R. C. and F. Murad. "Adrenocorticotropic Hormone: Adrenocortical Steroids and Their Synthetic Analogs: Inhibitors of Adrenocortical steroid biosynthesis." in Gilman, A. G. et al (Editors). "The Pharmacological Basis of Therapeutics." 7th edition, 1985. MacMillan Publishing Co., New York.)

SUMMARY OF THE INVENTION

Accordingly, it is an objective of the present invention to provide a new, highly significant use for 16-epiestriol as an anti-inflammatory drug.

It is a further object to provide a drug with minimal estrogenic and mineralocorticoid activity for use in treating the inflammatory signs and symptoms of rheumatoid arthritis and other diseases with an inflammatory component.

Other objectives and a fuller understanding of the present invention may be had by referring to the following description and claims taken in conjunction with the accompanying drawings and tables.

The present invention overcomes the deficiencies of the prior art and achieves its objectives by employing 16-epiestriol as an anti-inflammatory agent.

BRIEF DESCRIPTION OF THE DRAWINGS

In order to facilitate the understanding of the present invention reference will now be made to the appended FIGURE. The FIGURE should not be construed as limiting the invention, but is exampelary only. The FIGURE shows the anti-inflammatory activity of 16-epiestriol, the efficacy of 16-epiestriol as an anti-inflammatory agent being demonstrated by reduced paw edema (% change in paw volume) in rats treated with this agent compared to those that were not treated or those treated with twice the dose of cortisol in the carrageenin-induced inflammation model.

DESCRIPTION OF THE PREFERRED EMBODIMENT

The chemical compound 16-epiestriol, the new use of which is the subject of the present invention, is a known compound and is described at Entry 3565 of the 10th edition of the Merk Index.

The compound is known as Estra-1,3,5(10)-triene-3,16$\beta$,17$\beta$-triol; $\Delta$1,3,5-estratriene-3,16$\beta$,17$\beta$-triol; 16-epiestriol; or as Actriol. The compound has the empirical formula:

$C_{18}H_{24}O_3$; mol. wt. 288.37.

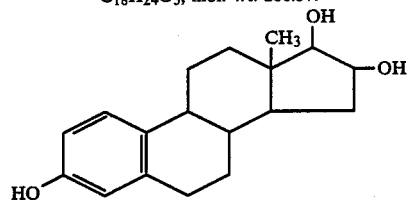

It is further known as 16$\beta$-estriol; 1,3,5,(10)-estratriene-3,16$\beta$,17$\beta$-triol; 3,16$\beta$,17$\beta$-trihydroxy $\Delta$1,3,5-estratriene; and trihydroxy-estrin(16$\beta$).

The method of isolation and synthesis of the compound and its chemical and physical properties are described in Marrian and Bauld [Biochem. J. 58, xxvi (1954); 59, 136 (1955)]; Watson, Marrian, ibid. 63, 64 (1956); Diezfalusy, Halla, Acta Endocrinol. 27, 303 (1958); Biggerstaff, Gallagher, J. Org. Chem. 22, 1220 (1957) Huffman [J.A.C.S. 66, 150 (1944); 69, 1835 (1947)]; Huffman, Gollman [Endocr. 41, 12 20 (1947)] and U.S. Pat. No. 3,002,009 issued Sept. 26, 1961 to Max M. Huffman.

The anti-inflammatory nature of 16-epiestriol was confirmed in the course of the following described experiments where parts are by weight unless otherwise indicated.

EXAMPLES

Five groups of rats with a body weight of approximately 200 grams per rat were administered intraperitoneally as follows:

Group One—0.5 milliliters of 1% carboxymethylcellulose in water. (The carrier vehicle)

Group Two—20 milligrams of cortisol/kilogram body weight in 0.5 milliliters of vehicle.

Group Three—20 milligrams of 16-epiestriol/kilogram body weight in 0.5 milliliters of vehicle.

Group Four—10 milligrams of 16-epiestriol/kilogram body weight in 0.5 milliliters of vehicle.

Group Five—40 milligrams of 16-epiestriol/kilogram body weight in 0.5 milliliters of vehicle.

The test was administered in accordance with the following protocol:

One hour prior to induction of inflammation, each animal was given an intraperitoneal injection of the appropriate dose as described above. Immediately prior to induction of the inflammation, the volume of the right rear paw of each animal was measured by a mercury plethysmograph. The inflammation was induced at time "0" by an injection of 0.05 milliliters of 1% suspension of carrageenin into the right rear paw of each animal. At times +1 hour, +2 hours, +3 hours, and +5 hours the right rear paw volume was again measured.

The FIGURE illustrates the percent change in paw volume for the untreated control, the cortisol treated, and the 10 milligram of 16-epiestriol/kilogram body weight treated rats. The results are indicated in Table I as milliliters change in paw volume at each testing. In Table II the percent volumetric changes in paw value at each test time are set forth.

It will be noted from the data that all three dosages of 16-epiestriol were statistically and biologically significantly reduced inflammation at the five hour test. ($P<0.001$ by Students t-test). In addition, the 10 milligram dose of 16-epiestriol was statistically and biologically significantly more effective than the 20 milligram dose of cortisol at reducing the inflammation at the five hour test. ($P<0.001$ by Student's t-test). The above data clearly indicates the effectiveness of 16-epiestriol in reducing inflammation and suggests its potential use in the effective treatment of rheumatoid arthritis and other diseases or conditions with an inflammatory component.

TABLE I

ANTI-INFLAMMATORY EVALUATION OF
16-epi estriol
MODEL: Carrageenin inducted rat paw inflammation.

| TREATMENT GROUP | MLS CHANGE IN PAW VOLUME (+/−S.E.) | | | | |
|---|---|---|---|---|---|
| | 0 HOUR | 1 HOUR | 2 HOUR | 3 HOUR | 5 HOUR |
| Untreated Controls | 0.0 | 0.19 | 0.64 (0.09) | 1.08 (0.09) | 1.13 (0.06) |
| Treated Cortisol (20 mg/kg) | 0.0 | 0.19 | 0.40 (0.09) | 0.65 (0.11) | 0.89 (0.11) |
| Treated 16-epi estriol (10 mg/kg) | 0.0 | 0.22 | 0.59 (0.05) | 0.71 (0.05) | 0.50 (0.06) |
| Treated 6-epi estriol (20 mg/kg) | 0.0 | 0.17 | 0.44 (0.05) | 0.65 (0.04) | 0.48 (0.05) |
| Treated 16-epi estriol (40 mg/kg) | 0.0 | 0.21 | 0.62 (0.09) | 0.79 (0.12) | 0.58 (0.08) |

Sample size: Untreated Control - 10
All Treatments - 8/treatment

TABLE II

ANTI-INFLAMMATORY EVALUATION OF
16-epi estriol
MODEL: Carrageenin inducted rat paw inflammation.

| TREATMENT GROUP | % CHANGE IN PAW VOLUME (+/−S.E.) | | | | |
|---|---|---|---|---|---|
| | 0 HOUR | 1 HOUR | 2 HOUR | 3 HOUR | 5 HOUR |
| Untreated Controls | 0.0 | 15.1 | 49.8 (6.0) | 84.9 (6.0) | 89.6 (4.0) |
| Treated Cortisol (20 mg/kg) | 0.0 | 14.7 | 31.5 (7.5) | 51.4 (9.3) | 69.6 (9.0) |
| Treated 16-epi estriol (10 mg/kg) | 0.0 | 16.2 | 43.1 (3.4) | 52.3 (4.1) | 37.0 (4.6) |
| Treated 16-epi estriol (20 mg/kg) | 0.0 | 11.9 | 30.8 (3.1) | 45.3 (2.6) | 33.1 (3.2) |
| Treated 16-epi estriol (40 mg/kg) | 0.0 | 15.1 | 44.4 (6.1) | 57.0 (8.2) | 41.9 (6.1) |

Sample size; Untreated Control - 10
All Treatments - 8/treatment

The application of 16-epiestriol as an anti-inflammatory agent could take the form of derivatives such as:
16-epiestriol-17-acetate;
16-epiestriol-16,17-diacetate;
16-epiestriol-3,16,17-triacetate;
16-epiestriol-16,17-dipropionate;
16-epiestriol-17-pivalate;
16-epiestriol-17-cypionate;
16-epiestriol-acetonide;
16-epiestriol-sodium succinate;
16-epiestriol-sodium phosphate;
and any and all other derivatives.

The 16-epiestriol or derivative is administered in an anti-inflammatory amount by any convenient method.

Preferred methods of administration are, topically, orally, subcutaneous injections or implantation; intramuscular injections; intra-articular injections, and other routes. The effective amount is administered in a pharmaceutically safe formulation with a carrier.

The preferred dosage range of the compositions of the present invention is about 5 mg/kg to about 100 mg/kg of body weight. Reduced dosages for children and infants are preferred. Administration may be repeated during a 24-hour period.

Dosages for administration according to this invention may be compounded into oral dosage forms such as tablets, capsules, and the like. This done by combining the compounds with conventional carriers and other excipients, such as magnesium carbonate, magnesium stearate, talc, sugar, lactose, pectin, dextrin, starch, gelatin, tragacanth, methyl cellulose, sodium carboxymethyl cellulose, low melting wax, cocoa butter, and the like. Diluents, flavoring agents, binders, tablet-disintegrating agents and the like may also be compounded with the compositions of the present invention. Active ingredients in these compositions, whether solid or liquid, will be at least sufficient to impart anti-inflammatory activity in vivo after oral or parenteral administration.

The dosage requirements vary with the particular compositions employed, the route of administration, the severity of symptoms presented, and the particular subject being treated. Treatment will generally be initiated with small dosages less then the optimum dose of the compound. Throughout, the dosage may be increased until the optimum effect under the circumstances is reached. In general, the tangible embodiments of invention are most desirably administered at a concentration that will generally afford effective results without causing any harmful or deleterious side effects. The dose will vary depending on these and other such factors which a person skilled in the art will recognize.

Although a specific preferred embodiment of the present invention has been described in the detailed description above, the description is not intended to limit the invention to any particular forms or embodiment disclosed herein, since they are to be recognized as illustrative rather than restrictive. It will be obvious to those skilled in the art that the invention is not so limited. The invention is declared to cover all changes and modification of the specific examples of the invention herein disclosed for purposes of illustration which do not constitute departures from the spirit and scope of the present invention.

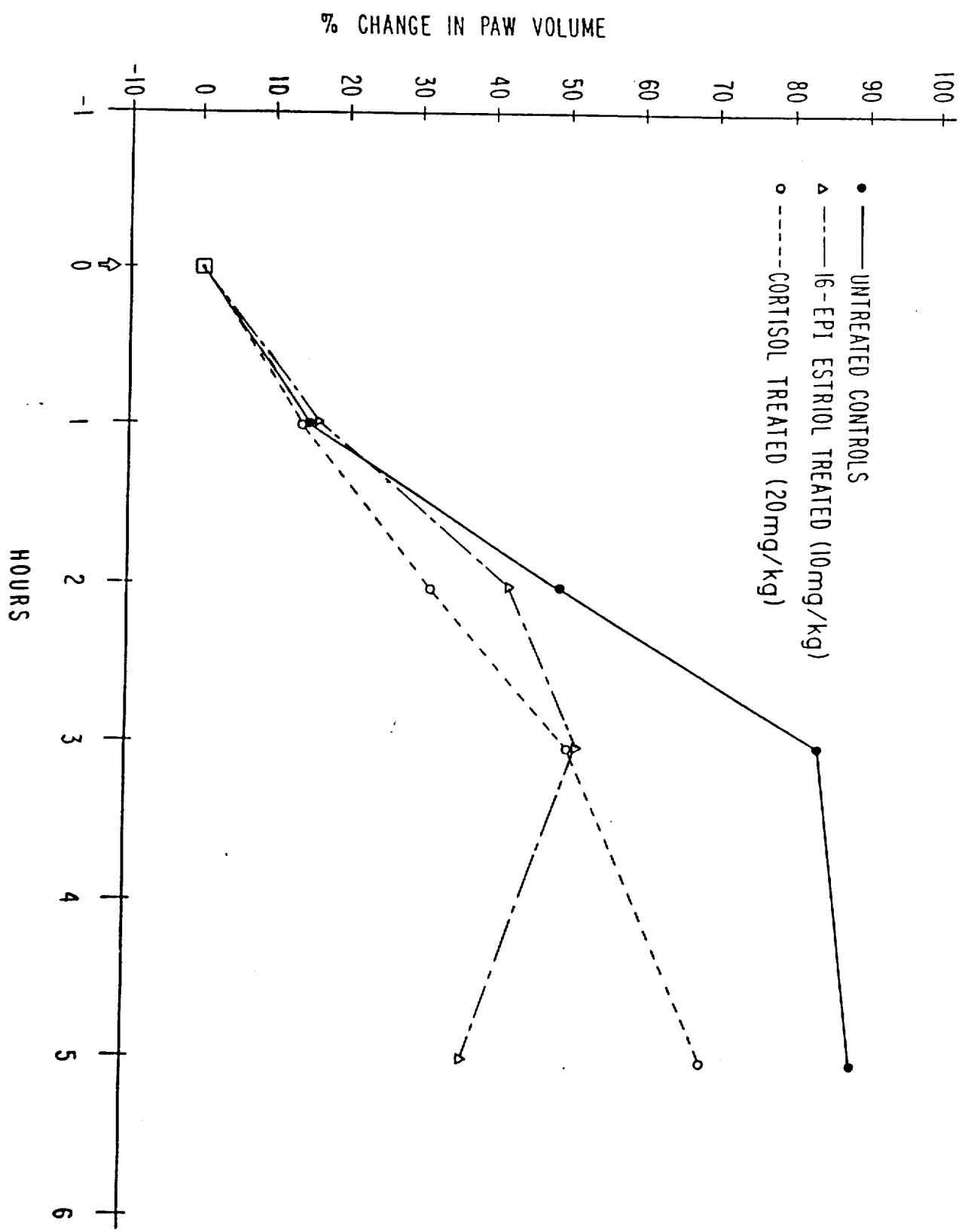

What is claimed is:

1. A method for the treatment of inflammation in a mammal which comprises administration of an anti-inflammatory effective amount of 16-epiestriol to said mammal.

2. A method according to claim 1 wherein the amount of 16-epiestriol is sufficient to prevent, inhibit, and/or reduce inflammation in animal tissue.

3. A method according to claim 1 wherein the 16-epiestriol is administered in a pharmaceutical formulation in combination with a carrier.

4. A method according to claim 3 wherein the mammal is a human.

* * * * *

UNITED STATES PATENT AND TRADEMARK OFFICE
CERTIFICATE OF CORRECTION

PATENT NO. : 4,795,747   Page 1 of 2

DATED : January 3, 1989

INVENTOR(S) : Neal S. Latman; Vimal Kishore and Brent C. Bruot

It is certified that error appears in the above-identified patent and that said Letters Patent is hereby corrected as shown below:

The drawing should be as shown on the attached sheet.

Signed and Sealed this

Ninth Day of January, 1990

*Attest:*

JEFFREY M. SAMUELS

*Attesting Officer*   *Acting Commissioner of Patents and Trademarks*